United States Patent [19]

Turner et al.

[11] Patent Number: 4,966,580

[45] Date of Patent: Oct. 30, 1990

[54] ORAL FEEDING APPLIANCE

[75] Inventors: John J. Turner; Mary J. A. Turner, both of Liverpool, England

[73] Assignee: National Research Development Corporation, London, England

[21] Appl. No.: 382,021

[22] Filed: Jul. 19, 1989

Related U.S. Application Data

[63] Continuation of Ser. No. 191,180, May 6, 1988, abandoned, which is a continuation-in-part of Ser. No. 79,775, Jun. 29, 1987, Pat. No. 4,813,933.

[30] Foreign Application Priority Data

Oct. 29, 1985 [GB] United Kingdom ................. 8526631
Jan. 16, 1986 [GB] United Kingdom ................. 8600988

[51] Int. Cl.5 ............................................. A61M 31/00

[52] U.S. Cl. ......................................... 604/67; 604/79; 215/11.4; A61M/31/00

[58] Field of Search .................................... 604/65-67, 604/77, 79; 215/11.4

[56] References Cited

U.S. PATENT DOCUMENTS

| | | | |
|---|---|---|---|
| 2,960,088 | 11/1960 | Witz | 215/11.4 |
| 3,126,002 | 3/1964 | Owens | 128/861 |
| 3,587,934 | 6/1971 | Elmore et al. | 222/529 |
| 3,669,101 | 6/1972 | Kleiner | 604/77 |
| 4,217,993 | 8/1980 | Jess et al. | 604/65 |
| 4,301,934 | 11/1981 | Forestal | 215/11.4 |
| 4,463,859 | 8/1984 | Greene | 215/11 R |

FOREIGN PATENT DOCUMENTS 2181958 5/1987 United Kingdom .

*Primary Examiner*—Randall L. Green
*Assistant Examiner*—Randy Shay
*Attorney, Agent, or Firm*—Cushman, Darby & Cushman

[57] ABSTRACT

A device for administering oral fluid to a patient from a container (18) has a nipple (14) connected to the container (18) by a tube (16). The nipple (14) is held on the patient's tongue. A valve (22) opens in response to the patient sucking or pressing the nipple to initiate a flow of fluid in the tube (16). A detector (92) responds to this flow and switches on a peristaltic pump (90) for a period determined by the setting of a controller (102) to deliver positively a suitable bolus of 2 to 6 ml to the patient. To give the patient time to swallow the bolus, the detector (92) is inhibited for a predetermined delay period after termination of the bolus and over the same delay period, the tube (16) remains pinched or clamped.

12 Claims, 1 Drawing Sheet

ORAL FEEDING APPLIANCE

CROSS-REFERENCE TO RELATED APPLICATIONS

This is a continuation of application Ser. No. 07/191,180, filed May 6, 1988, which was abandoned upon the filing hereof, which was a continuation-in-part of application Ser. No. 07/079,775 filed June 29, 1987 which issued as U.S. Pat. No. 4,813,933.

FIELD OF THE INVENTION

The present invention relates to apparatus for administering oral fluids.

BACKGROUND OF THE INVENTION

The monitoring of an adequate intake of fluids is vital to the care of all who are ill or who, because of physical or mental disability, have an impaired ability to drink normally. Individual feeding of such patients is time consuming and imposes a great strain on nursing resources. Alternative methods of administering fluids are intravenous and nasal tubes and such alternatives may be used inappropriately because of lack of a suitable system or facility for the administration of oral feeds.

U.S. Pat. No. 4301,934 describes an infant feeding device in which a teat is connected by a tube to an inverted feeding bottle. The infant can grasp the teat at will and place it in his or her mouth. The teat protrudes from a rigid disc which is too large to enter the infant's mouth, so avoiding any risk of the infant swallowing the teat. In the case of invalids, such an arrangement would not be satisfactory as the patient may not be able to place a feeder in his or her mouth or even may be of a mind to reject the feeder.

It has recently been proposed in UK Patent Application No. 2181958A to provide a device for administering oral fluid to a patient comprising a nipple, a soft reticulate mouthpiece shaped to be received between the nipple and the teeth or gums of the patient to hold the nipple over the patient's tongue, a container for the oral fluid, the container being at a higher level than the patient's head, and a tube leading from the container to the nipple, the latter containing a valve which prevents the fluid from flowing freely out of the nipple but which is operable by the sucking action of the patient so that the oral fluid flows out of the nipple so long as the patient continues to suck.

However, some patients who are extremely ill may be unable to maintain a sustained suction action sufficient to permit sufficient oral fluid to be administered to the patient.

SUMMARY OF THE INVENTION

Thus, the present invention resides in apparatus for administering oral fluid to a patient comprising a nipple, means for holding the nipple in the patient's mouth, a container for oral fluid, a tube leading from the container to the nipple, and means responsive to patient action on the nipple for metering the quantity of fluid flowing out of the nipple.

Preferably, the metering means comprises a pump and control means for the pump, the control means including a sensor responsive to an initial patient-induced flow int he tube and adapted to switch on the pump for a predetermined period to supply to the nipple a quantity of oral fluid determined by the said period.

Advantageously, inhibit means are provided to prevent reactivation of the pump before a predetermined delay has elapsed following switching off of the pump. This delay period is selected to give the patient time to swallow one bolus before the next can be delivered.

Conveniently, the holding means comprises a mouthpiece shaped to be received between the lips and the teeth or gums of the patient to hold the nipple in the patient's mouth.

The container can be supported on a stand or otherwise, so that the container is at a level slightly above the patient's head, whereby the fluid can be delivered to the nipple under gravity.

The nipple or the tube preferably contains a valve to prevent the fluid from flowing freely out of the nipple. Such valve may be operable by the patient by the application of suction to the nipple and/or by an associated manipulation of the nipple by the patient, e.g. by tongue pressure.

Preferably, the mouthpiece is soft and is adapted to be received between the lips and the gums. It is of such a design that it can be retained by the dentulous, the edentulous or by a patient wearing dentures. Advantageously, the mouthpiece is reticulate or otherwise air pervious so that the mouthpiece does not impede mouth breathing.

It is recommended that the nipple should be positioned on the mouthpiece such that the nipple will lie on the tongue to stimulate a sucking action by the patient.

Conveniently, the container is closed by a rubber diaphragm which can be pierced by a hollow non-coring needle on the inlet end of the tube and which is self-resealing so that the hollow needle can be withdrawn and re-inserted several times, rather like the closure of a conventional blood transfusion or intravenous supply. This enables the tube to be disconnected, when not in use, and to be flushed with a suitable disinfectant, such as a mouthwash liquid.

Preferably, the stand incorporates a receptacle to receive a disinfectant, such as mouthwash liquid, in which the mouthpiece can be placed when not in use.

The container may have a closeable top to enable it to be filled just before use or to be re-filled, if desired. Alternatively, the container could be a pre-pack.

The nipple and the tube, and possibly the container of the apparatus of the invention would normally be disposable. In many cases, they would be discarded no longer than twenty four hours after first being put in use, but would be used several times within this period, the mouthpiece being immersed in disinfectant when not in use and the tube being flushed with disinfectant between periods of use.

BRIEF DESCRIPTION OF THE DRAWING.

The invention will be further described, by way of example, with reference to the accompanying drawings, in which.

DESCRIPTION OF THE PREFERRED EMBODIMENTS

Figure 1:
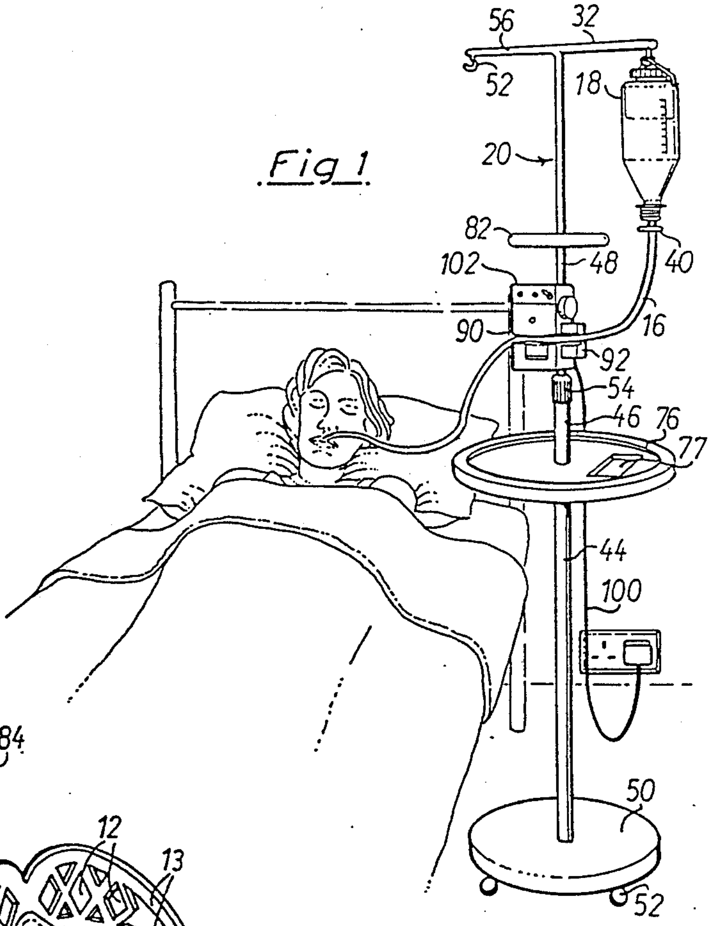
FIG. 1 is a somewhat diagrammatic perspective view of apparatus for administering oral fluid in accordance with the invention.

The apparatus shown in the drawings comprises a soft mouthpiece 10 which is designed to be retained between the lips and the gums of the patient and is so shaped as to be soft and comfortable. The mouthpiece 10 is suitably designed to be air pervious so as not to inhibit the patient from breathing through the mouth. To this end it may be designed as a lattice-like structure to define openings 12. So that the mouthpiece 10 will fit patients with different sized and shaped mouths, it is made extremely flexible and includes two tapering side portions 13 at each side, these side portions converging towards one another but without touching one another in the free state.

The mouthpiece 10 is provided with a nipple 14 which projects sufficiently far for it to be received on the tongue of the patient. The nipple 14 is preferably of a somewhat flattened or oblate shape. It is connected by a flexible tube 16 to a container or reservoir 18 which can be suspended from an arm 32 of a stand 20 so as to be at a level slightly higher than the level of the patient's head. Oral fluiid in the reservoir 18 is thus delivered to the nipple 14 at slight excess pressure but, to prevent the fluid from dribbling out of the nipple, the nipple is provided with a valve 22 which is designed to remain closed under a slight pressure head but to be opened when the patient applies suction to the nipple 14.

The mouthpiece 10 can be designed to provide a maximum degree of comfort since it does not need to be very strong.

Parts of the apparatus of the invention, that is to say, the mouthpiece 10, the tube 16 and the container 18, will normally be designed to be disposable and thus the reservoir or container 18 will usually be a plastics bottle having a filler cap. It is even possible for the reservoir to be prefilled provided that the fluid is properly sterilized.

Whilst the reservoir 18 is shown suspended from a hook on the arm 32 of the stand 20 it is not necessary to provide a separate stand. The reservoir 18 could, for example, be suspended from the head of the patient's bed.

The lower end of the reservoir 18 is closed by a rubber diaphragm (not visible) which can be pierced by a pointed hollow, preferably non-coring needle (also not shown). To this end, the hollow needle is formed integrally with a handle 40. The tube 16 is attached to the hollow needle. The hollow needle, together with the handle 40, will usually be moulded from plastics material. The reservoir 18 can be calibrated to enable the amount of oral fluid in the reservoir 18 to be measured.

The rubber diaphragm closing the lower end of the reservoir 18 is of a kind which re-closes when the needle is removed, so enabling the tube 16 to be disconnected from the reservoir 18 when not in use.

In an alternative arrangement, the containers 18 are pre-packs and the tube 16 can simply be plugged into a container.

For metering the oral fluid to the patient, a peristaltic pump 90 is provided. This pump is mounted on the stand column 44 at a convenient height but below the container 18. A flow detector 92 is also provided and this is conveniently attached to the pump 90 as shown. The peristaltic pump 90 is of conventional design mechanically and has rollers 94 which can engage and pinch the tube 16 and which are journalled about the periphery of a rotor (not shown) driven by an electric motor 96 (shown diagrammatically in dotted lines). When the rotor is rotated, the rollers 94 pinch and roll along the tube 16 to positively displace the oral fluid in the tube 16 towards the nipple 14. The rollers 94 co-operate with a displaceable clamping member 98 which can be advanced by means of a solenoid 99 (shown diagramatically by dotted lines) to a clamping position, in which the tube 16 is pinched, from the release position in which the tube 16 is not pinched. In the release position, the tube 16 can be inserted and removed and fluid flow is permitted in the tube 16 when the motor 96 is switched off. The peristaltic pump 90 is supplied with power through a mains lead 100.

The flow detector 92 is preferably of the optical laser type. Such a detector is capable of detecting very slight movement of ions or of particles in the fluid and thus can respond to a small fluid flow in the tube 16 so long as the oral fluid is not pure water. As soon as the patient sucks on the nipple 14 with the clamping member 98 retracted, the resulting fluid flow in the tube 16 is detected by the detector 92 which causes the peristaltic pump 90 to be switched on as will be described further hereinafter.

Instead of an optical laser-rype flow detector, a photo-electric detector may be used. Such a photo-electric detector can co-operate with a sight glass inserted in the tube 16, the sight glass being one by means of which fluid flow can be observed as drops falling past the sight glass.

A further possibility is for the flow detector to be a sensitive pressure transducer which may be disposed in or adjacent the mouthpiece and which responds to a small pressure change which takes place when the patient sucks on the nipple 14.

The apparatus includes a controller 102 which is also conveniently mounted on the peristaltic pump 90. The controller 102 is connected to the pump motor 96, to the solenoid 99 and to the flow detector 92 and contains a microprocessor 104. The controller 102 is provided with an on-off switch 106 and with pilot lamps 108 of which two are shown by way of example. The controller 102 could also be provided with a digital display panel (not shown) for displaying information relevant to its mode of operation. An adjustment knob 110 serves to adjust the metered amount or bolus of oral fluid.

The microprocessor 104 is so programmed as to enable the device to operate as hereinafter described. In the switched-off state, the clamping member 98 is retracted so that the tube 16, which has already been connected to the container 18 and to the mouthpiece 10 is described above, can be inserted between the clamping member 98 and the pump rollers 94. When the controller 102 has been suitably adjusted and switched on, the apparatus is ready to operate. It is preferable to insert the mouthpiece 10 in the patient's mouth before switching on to reduce the risk of spillage.

When the patient sucks on the nipple 14, the valve 22 opens as described above and some oral fluid flows from the container 18 into the patient's mouth. This fluid flow is immediately detected by the detector 92 which sends a signal via a transmitter or interface (not shown) to the microprocessor 104. The latter causes the solenoid 99 to be energised, which advances the clamping member 98 towards the rollers 94 and pinches the tube 16 therebetween. Simultaneously, the motor 96 is energised to create a positive pumping action in the tube 16. The motor 96 is rotated at a predetermined speed (which may be pre-adjustable to provide any delivery rate, say, between 6 and 45 ml per minute) so that the rate of delivery of oral fluid to the patient is fixed. After the lapse of a predetermined but adjustable period of time, the motor 104 is switched off, whereby a bolus of predetermined magnitude is delivered to the patient. By way of example, a bolus of 2 to 6 ml can be delivered over a period of 1 to 3 sec. It has been found that a patient incapable of taking in an adequate supply of oral fluid by normal means can accept such a bolus. The switch-on period of the pump and therefore the magnitude of the bolus can be adjusted by means of the knob 110.

It is desirable that there be a minimum delay between the termination of delivery of one bolus and the commencement of delivery of the next bolus. Accordingly, the illustrated apparatus includes means whereby the delivery of fluid to the mouthpiece 10 is inhibited over a predetermined delay period of, say, 5 to 20 sec. following switching off of the motor 94. To this end, the microprocessor 104 is programmed to prevent any signal from the flow detector 92 from causing the motor 96 to be re-energised until the delay period has elapsed. This delay period may be adjusted by means of another control knob (not shown). Also, instead of the solenoid 99 being released simultaneously with switching off of the predetermined delay has elapsed. Thus the tube 16 remains pinched between the clamping member 98 and the rollers 94 which are no longer rotating and fluid flow in the tube 16 is positively prevented.

A further manual switch (not shown) can be provided for optionally energising the solenoid 99 to prevent fluid flow and response of the apparatus whilst the apparatus is being set up or dismantled.

Instead of the solenoid 99 being operated during the predetermined delay, a separate electrically operated tube clamp could be provided.

The controller 102 could be provided with a keyboard (not shown) to enable the microprocessor 104 to be pre-programmed, e.g. as to the speed of the pump 96 and/or the delay in release of the solenoid 99 and/or the switch-on period of the pump 96. In the last case, the knob 110 would be omitted. In a more sophisticated form of the invention, the microprocessor may be adapted to indicate the total volume of fluid administered and could be adapted to monitor the amount of urine from the patient to give a total liquid balance indication.

The apparatus of the present invention is not a forced delivery system inasmuch as the delivery is stimulated by the patient. If the actual liquid intake is considered to be clinically inadequate, an intensive care technique for administering fluid must be adopted in place of the apparatus of the invention.

The stand 20 comprises an upright column 44 formed of telescopic tubes 46 and 48. The lower tube 46 is provided with a heavy base 50 having castors 52 on its lower side. Upper inner tube 48 is slidably received in lower outer tube 46 and can be locked in any desired adjusted position within limits by means of a collet 54.

The arm 32 and another arm 56 are attached to the upper end of the upper tube 48. The tube 16 can be detached from the reservoir 18 and instead attached to a disinfectant bottle (not shown) suspended from a hook 52 on the arm 56. Like the reservoir 18, the bottle is closed at its lower end by a rubber diaphragm which can be pierced by the hollow needle 38. The bottle can be re-filled with disinfectant as necessary and its top can be closed by a screw-top lid.

Whilst it is preferable for the reservoir 18 to be of clear transparent, uncoloured plastics material in order that its contents can be observed accurately, it is preferable to make the bottle for disinfectant of a distinctive colour and/or a distinctive shape and/or distinctively marked, yet still sufficiently transparent to enable the level of the disinfectant to be observed.

A receptacle (not shown) can be attached to the column 44 at a convenient height for adequate observation in use and is shaped to receive the mouthpiece 10 when the device is not in use. A transparent lid is provided for closing the receptacle and has resilient tabs for releasably holding the lid closed. The front wall of the receptacle is formed with a notch through which the tube 16 passes. The receptacle will normally contain a suitable disinfectant so that the mouthpiece remains immersed in the disinfectant when the device is not in use. The lowermost part of the receptacle is provided with a stopper which can be removed to enable the receptacle to be drained and cleaned.

Conveniently, a table 76 is attached to the lower tube 46 of the stand 20 and has an aperture 77 shaped to receive a self-sealing expandible disposable collection bag (not shown) of lightweight foil plastics or other suitable material. The self-sealing aperture of the bag will receive the tube 16 and allow collection of the antiseptic fluid and other fluid residues from the tube 16. A second table 82 is situated above the table 76 and is also attached to the lower tube 46. The table 82 can be provided with one or more apertures to locate a bowl or receiver (not shown) containing a suitable fluid ror rinsing antiseptic residues from the mouthpiece 10 prior to insertion in the patient's mouth. Bottles of disinfectant, medicaments etc., which the nursing staff require to use from time to time, can be placed on the tables 76, 82.

A "Luer" or similar type of locking joint 83 allows the mouthpiece 10 to be detached from the tube 16, in order to allow all antiseptic and other fluid residues to be drained from the tube and the mouthpiece before insertion into the patient's mouth and the elimination of rehydrating fluids.

After use of the apparatus according to the invention, the tube 16 can be detached from the reservoir 18 and instead be attached to the bottle of disinfectant. The mouthpiece is then lowered to a point just above the collecting bag, whereupon a sufficient pressure is developed at the valve 22 to open the valve so that disinfectant will pass through the tube 16 and mouthpiece 10 to flush out the oral fluid remaining therein. Thereafter, the mouthpiece 10 is placed in its receptacle.

Before the next use of the apparatus, the tube 16 is detached from the disinfectant bottle and from the mouthpiece 10 and the lower end of the tube 16 inserted in the collection bag to drain at least some of the disinfectant out of the tube. Thereafter, the tube is attached to the reservoir 18 and, with the end of the tube still held in the bag, the tube clamp is opened in order that some of the oral fluid from the reservoir 18 can be used to purge any remaining disinfectant from the tube 16. The mouthpiece 10 is then re-attached and the device is ready for use by the patient as described above.

Figure 2:
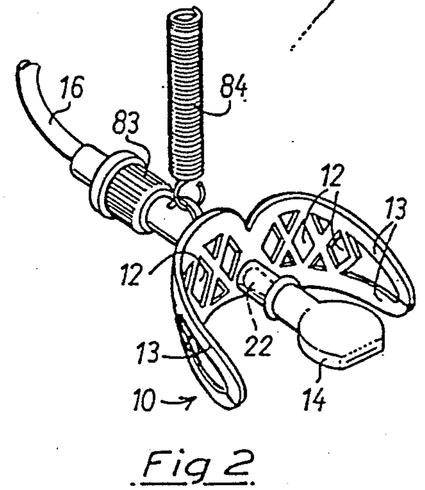
FIG. 2 is a perspective view of the mouthpiece of the apparatus.
Figure 3:
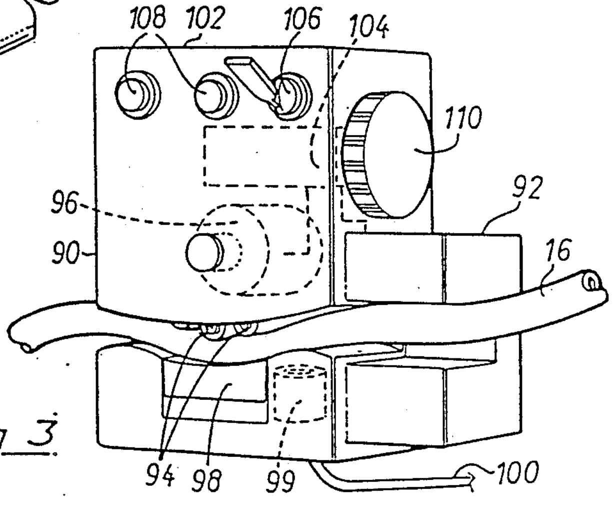
FIG. 3 is a perspective view of the peristaltic pump of the apparatus.

It is advantageous for the mouthpiece 10 to be restrained from falling on the floor or becoming lost in the bedclothes, should it be removed by the patient from his mouth. To this end, a light elastic cord or spiral spring 84 (FIG. 2) extends from a rod (not shown) suspended from the stand 20 and can be releasably hooked onto the mouthpiece. In a preferred arrangement, this rod is attached by one end to the stand by means of a swivel joint.

The apparatus of the present invention is particularly useful for patients who have undergone major surgery and have necessarily been fed intravenously for several days and who must be weaned back on to ordinary foods. Such patients are usually extremely ill and drowsy and unable to drink fluids without assistance. The use of the device of the invention in such circumstances frees the nursing staff for other duties.

It will be appreciated that the apparatus of the present invention is useful for hospital patients who have impaired thirst responses or are not motivated to drinking normally by reason of underlying illness, pain, sedative drugs or immobility. It is particularly applicable to older patients who are more prone to dehydration. It is also suitable for some groups of post-operative patients and for terminally ill patients.

We claim:

1. Apparatus for administering ingestible oral fluid to a patient comprising:
- a nipple;
- means for holding the nipple in the patient's mouth;
- a container for the oral fluid;
- a tube leading from the container to the nipple; and
- metering means responsive to patient action on the nipple to initiate fluid flow out of the nipple, said metering means acting to continue said flow in a predetermined manner independent of continuous patient action.

2. Apparatus according to claim 1 in which one of the nipple and the tube contains a valve normally closed to prevent the fluid from flowing freely out of the nipple and operable to open to allow such flow.

3. Apparatus according to claim 2 in which the valve is operable by the patient.

4. Apparatus according to claim 2 in which the valve is operable by the application of suction to the nipple.

5. Apparatus according to claim 2 in which the valve is actuable by the application of tongue pressure to the nipple.

6. Apparatus according to any claim 1 in which said holding means comprises a mouthpiece shaped to be received between the lips and the teeth or gums of the patient to hold the nipple in the patient's mouth.

7. Apparatus according to claim 6 in which the mouthpiece is air pervious so that the mouthpiece does not impede mouth breathing.

8. Apparatus for administering ingestible oral fluid to a patient, comprising:
- a chamber adapted to be held in the patient's mouth, the chamber having a fluid inlet opening directed outwardly of the mouth when so held and a fluid inlet opening and a resilient wall directed inwardly of the mouth;
- a container for the oral fluid;
- a tube communicating said container with said inlet opening for fluid flow therethrough;
- and control means connected in said tube, said control means being operable in response to distortion of said resilient wall by patient oral action to initiate said fluid flow and to continue said flow, when initiated, in a predetermined metered manner independent of continuous oral action.

9. Apparatus for administering ingestible oral fluid to a patient comprising:
- a nipple;
- means for holding the nipple in the patient's mouth;
- a container for the oral fluid;
- a tube leading from the container to the nipple; and
- metering means responsive to patient action on the nipple to initiate fluid flow out of the nipple, said metering means acting to continue said flow in a predetermined manner independent of continuous patient action, the metering means including a pump and control means for the pump, the control means including a sensor responsive to an initial patient-induced flow in the tube and adapted to switch on the pump for a predetermined period to supply to the nipple a quantity of oral fluid determined by said period.

10. Apparatus according to claim 9 in which the pump is a peristaltic pump adapted to co-operate with said tube.

11. Apparatus according to claim 9 in which inhibit means are provided to prevent re-activation of the pump before a predetermined delay has elapsed following switching off of the pump.

12. Apparatus according to claim 11 in which the inhibit means includes means for closing off said tube during said delay.

* * * * *